(12) United States Patent
Aknin

(10) Patent No.: US 6,382,966 B1
(45) Date of Patent: May 7, 2002

(54) APPLIANCE FOR ORTHODONTIC TREATMENT

(76) Inventor: Jean-Jacques Aknin, 23, rue Clement Michut, 69100 Villeurbannc (FR)

( * ) Notice: Subject to any disclaimer, the term of this patent is extended or adjusted under 35 U.S.C. 154(b) by 0 days.

(21) Appl. No.: 09/674,326
(22) PCT Filed: May 5, 1999
(86) PCT No.: PCT/FR99/01064
§ 371 Date: Dec. 18, 2000
§ 102(e) Date: Dec. 18, 2000
(87) PCT Pub. No.: WO99/56657
PCT Pub. Date: Nov. 11, 1999

(30) Foreign Application Priority Data

May 5, 1998  (FR) ............................................ 98 05909

(51) Int. Cl.$^7$ ................................................. A61C 3/00
(52) U.S. Cl. ............................................. 433/10; 433/8
(58) Field of Search ............................. 433/3, 8, 10, 13, 433/17, 18, 20, 21, 22

(56) References Cited

U.S. PATENT DOCUMENTS

| | | | | | |
|---|---|---|---|---|---|
| 4,279,593 A | * | 7/1981 | Rohlcke | ........................ | 433/8 |
| 4,330,271 A | * | 5/1982 | Anderson | ....................... | 433/3 |
| 4,575,337 A | * | 3/1986 | Fijita | ............................ | 433/15 |
| 4,582,487 A | * | 4/1986 | Creekmore | .................... | 433/8 |
| 4,585,413 A | | 4/1986 | Wool | ............................. | 433/8 |
| 5,374,187 A | * | 12/1994 | Vashi | ............................. | 433/8 |

* cited by examiner

Primary Examiner—Gary E. O'Connor
(74) Attorney, Agent, or Firm—Oliff & Berridge, PLC

(57) ABSTRACT

This appliance comprises metal housings which are fastened by their base being glued to a defined tooth and of which those for the incisors, canines and premolars comprise a horizontal groove for receiving the arch wire, said groove issuing in the direction of the occlusal plane and being formed in an intermediate bridge connecting the base to an anterior wall, and ties, such as elastic rings, for tying the arch wire.

According to the invention, each of the housings for the incisors, canines and premolars comprises, for attaching an elastic ring for tying to the arch wire, and in the intermediate bridge, on one side, between the base and the groove for the arch wire, an anchoring flute issuing in the direction of the occlusal plane and, on the other side, between the base and the anterior wall, a horizontal groove issuing opposite the groove for the arch wire, while the anterior wall has a width and a height greater than those of the base and than those of the intermediate bridge, in order to mask this bridge and the elastic ring for tying the arch wire.

9 Claims, 6 Drawing Sheets

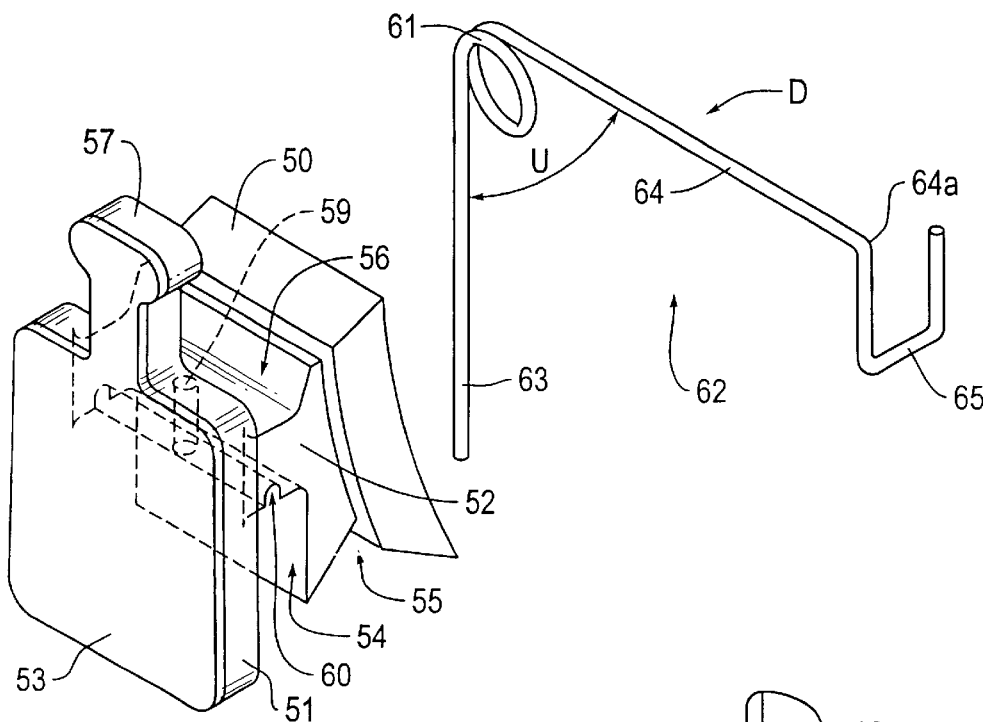
Fig. 7
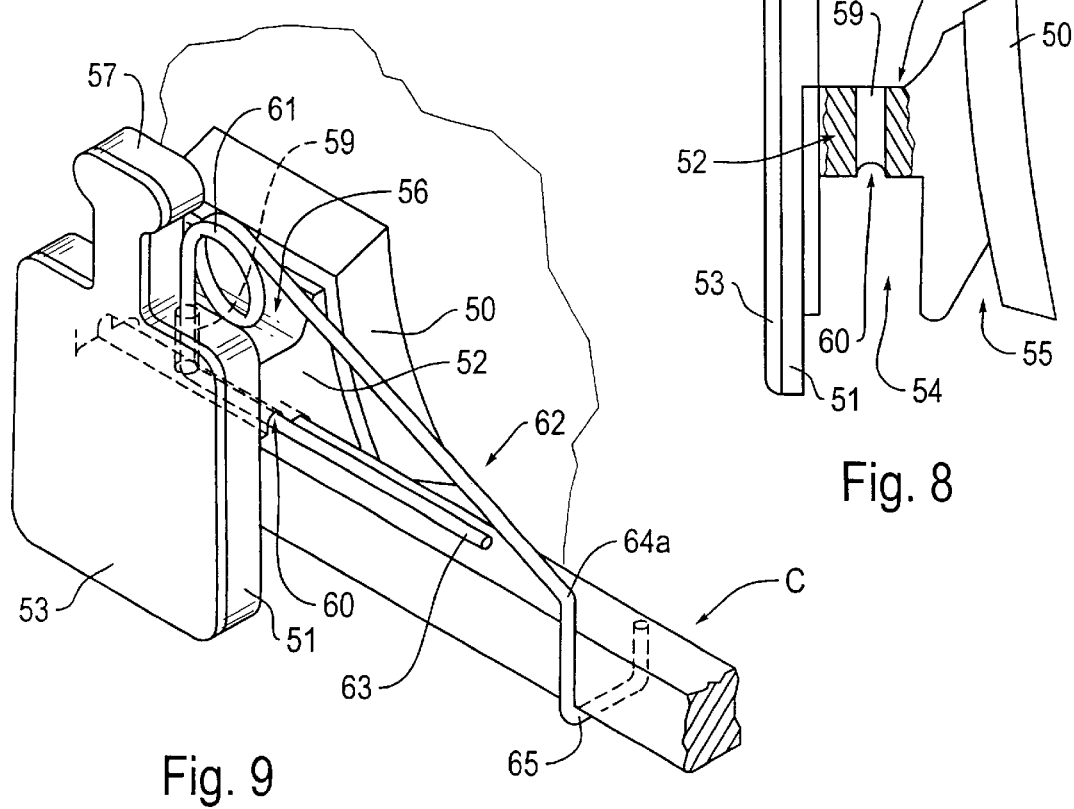
Fig. 8
Fig. 9

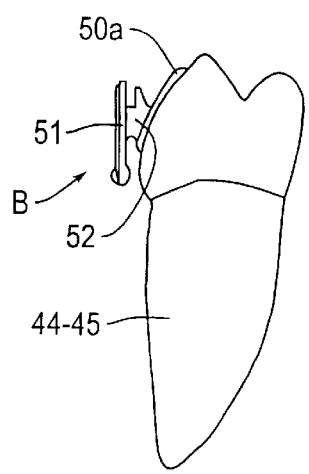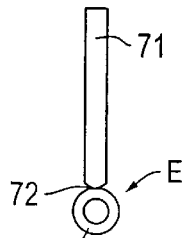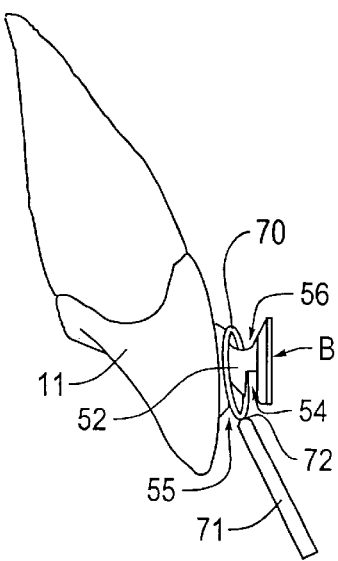
Fig. 10  Fig. 11  Fig. 12
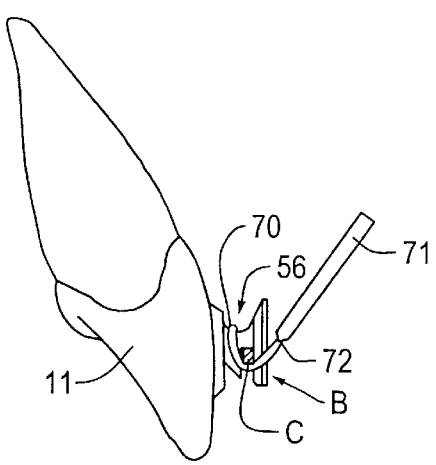
Fig. 13
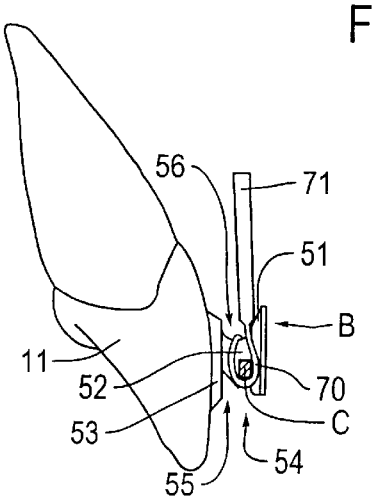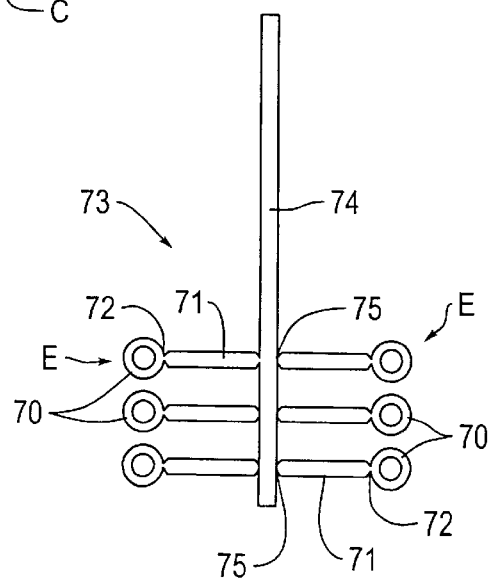
Fig. 14  Fig. 15

APPLIANCE FOR ORTHODONTIC TREATMENT

The invention relates, to an orthodontic dental appliance.

BACKGROUND OF THE INVENTION

In order to correct dental malformations both on the upper or maxillary arch and on the lower or mandibular arch, it is known to use appliances which, within the framework of orthodontic treatment, make it possible to straighten badly positioned teeth by imparting to them forces tending to straighten them axially, that is to say in a lateral plane or under "torque", that is to say in the anteroposterior plane.

Current appliances comprise, for each dental arch, housings or supports, also called brackets, which, glued to the inner or outer face of each of the teeth, comprise, as shown in the accompanying FIG. 1, on the one hand, a base b, in which is made a horizontal groove f capable of receiving an arch wire d which is composed of a nonoxidizing metal alloy and to which the base is connected by means of a tie consisting of a ring of synthetic material or a metal wire.

Each housing is specific to a tooth, and the horizontal slots made in the housings have an angulation relative to their base both in the frontal vertical plane and in the anteroposterior vertical plane. These angulations vary as a function of the teeth on which the housings must be arranged and of the intended straightening. Likewise, the arch wires are selected from a series of a plurality of arch wires differing from one another in the morphology of the dental arches and, as regards each dental arch, in the straightening forces which the branches provide. In practice, the metal arch wires have a more or less large round, square or rectangular cross section and are modified as treatment progresses.

In a distalization phase of some teeth, the ends of the arch wire are connected to means which impart to it a tensile force toward the rear, that is to say in the direction of the interior of the mouth, and are generated by external pericranial support means. As treatment progresses, the orthodontist adapts the force generated by the arch wire and those forces generated by possible intermaxillary connections between the maxillary corrective element and the mandibular corrective element, so as to adjust the repositioning of the teeth.

In some appliances, each arch wire is inserted horizontally into the grooves of the housings fastened to the maxillary teeth and to the mandibular teeth. Since each groove issues horizontally, the wire is held insufficiently, this being conducive to the version or axial rotation of the teeth during treatment and consequently slowing down the corrective effects of this treatment.

DESCRIPTION OF THE PRIOR ART

The same is true of appliances in which, as described in U.S. Pat. No. 5,374,187 and U.S. Pat. No. 4,585,413, the horizontal groove for receiving the arch wire is made in an intermediate bridge connecting the base to an anterior wall and issues vertically in the direction of the occlusal plane or of the gum. This is because, if the connection to the arch wire is not firm, has play or is made punctually, it makes it possible, under the straightening force imparted by the arch wire, for the tooth to tilt by pivoting about the resistant center of the latter, said center being located midway up the root. During treatment, the tooth pivots in one direction and the other, generating, on the root, stresses which may lead to resorption, that is to say to a reduction in its length, and even to the loss of the tooth.

One object of the invention is to overcome these disadvantages by ensuring a positive connection between housing and arch wire, making it possible, by means of a low straightening force, to straighten the tooth in a translational movement, or aggression, without any version of the root.

With current appliances, it is necessary, in the distalization phase, to make use of an extra-oral pericranial support appliance for generating the straightening forces on the arch wires. This solution is demanding for the patient and, above all, because of its pericranial support, sometimes causes headaches which may have an adverse effect on cranial and basicranial structural growth, particularly in young patients at risk who have disorders of the temporomaxillary joint or of vertebral statics.

Another object of the invention is to provide an orthodontic appliance which avoids any need for extra-oral pericranial support tractions.

Another disadvantage of this current type of appliance is its unesthetic nature, disclosed in FIG. 1. Specifically, even if each housing comprises an anterior face composed of ceramic or the like of the color of ivory, the metal arch wire forms a highly visible dark-colored girdle which attracts attention and mars the dental arch.

Likewise, the elastomeric ties connecting the housings to the arch wires gradually add to the unesthetic appearance, since, under the action of the saliva, they swell, lose color and become yellow.

Another object of the invention is to provide an appliance which has little adverse effect on the esthetic appearance of the dental arches.

Finally, because of its uneven shapes, each housing promotes a substantial retention of dental plaque both on its visible and on its nonvisible parts. This dental plaque gives rise to risks of leucomas, coloration, enamel stains and even decay.

Another object of the invention is to reduce the formation of dental plaque where it is formed and to make brushing easier.

SUMMARY OF THE INVENTION

The invention relates to an appliance which, for each in each case maxillary and mandibular dental arch, is composed:

of a series of arch wires forming a U-shaped arc, surrounding each dental arch and differing from one another in the straightening forces which their branches supply, said wires having a rectangular cross section, with their small sides parallel to the occlusal plane, of metal housings which are fastened by their base being glued to a defined tooth and of which those for the incisors, canines and premolars comprise a horizontal groove for receiving the arch wire, said groove issuing in the direction of the occlusal plane and being formed in an intermediate bridge connecting the base to an anterior wall, while the housings for the molars comprise a tunnel for positioning the end of the corresponding branch of the arch wire, of ties, such as elastic rings, for tying the arch wire in the grooves of the housings, and of means imparting, at least to the maxillary arch wire and in one treatment phase, a tensile force directed toward the rear.

According to the invention, each of the housings for the incisors, canines and premolars comprises, for attaching an elastic ring for tying to the arch wire and in the intermediate bridge, on one side, between the base and the groove for the arch wire, an anchoring flute issuing in the direction of the occlusal plane and, on the other side, between the base and the anterior wall, a horizontal groove issuing opposite the groove for the arch wire, while the anterior wall has a width and a height greater than those of the base and than those of the intermediate bridge, in order to mask this bridge and the elastic ring for tying the arch wire.

By means of this appliance, the arch wires are inserted from the occlusal part toward the gingival part, thus making the practitioner's task easier. The arrangement of the grooves for the elastic ring considerably improves the hold of the arch wires which can thus carry out more efficient dental correction, without unwanted movements.

The housings are very easy to clean, as are, moreover, the base and the intermediate bridge, since, where most of the housings are concerned, these parts are free of protuberances and various projections.

In esthetic terms, the anterior walls conceal from view not only the housing, but also part of the arch wire and the ties of the arch wire to the housing, thus doing away with the metallic appearance of current appliances.

When the tie is put in place, it is concealed completely by the anterior wall and therefore cannot, over time, impair the esthetic appearance of the appliance, for example by becoming yellow under the action of saliva.

In one embodiment, the tie formed by the elastic ring comprises two loops surrounding the parts of the arch wire which project longitudinally from the intermediate bridge, and these loops are obtained as a result of the elastic ring being put in place around the intermediate bridge, in the flute and in the groove of the housing, then, after the introduction of the arch wire into the groove, of the elastic ring being pivoted around the arch wire for the purpose of attaching its loop coming from the flute in the opposite groove.

By virtue of the two loops, the arch wire is wedged firmly in the groove in terms of vertical translation, horizontal translation and longitudinal translation, so that the tooth cannot pivot relative to said arch wire and, under the straightening force, can be displaced only in a translational movement parallel to itself, without any effect on its root.

In one embodiment, and for carrying out the straightening of complex pathologies, each housing for the canines and premolars comprises, in its part between the base and its anterior part, a vertical well issuing into the groove for the arch wire and forming, with a flute made in the bottom of said groove, an anchoring member for the bent end of one of the branches of a kickover spring for the axial straightening of the tooth, the other branch of this spring being provided with an end hook hooking onto the arch wire.

Thus, the straightening of a tooth by means of a housing of this type is carried out by the kickover spring which comes to bear with one of its branches on the arch wire and, by its other branch cooperating with the intermediate bridge, imparts the axial straightening force to the housing and therefore to the tooth to which this housing is fastened.

In one embodiment, the appliance comprises a maxillary arch wire for the bilateral distalization of the molars and canines, comprising, on each of its lateral branches, on the one hand, a helical spring which is arranged around said branch and the anterior end of which is connected to this branch by means of a weld arranged on a zone of this branch which is set back from the canine, while the posterior end of this spring comes to bear on the housing of a molar, and, on the other hand, a vertical hook which, projecting upward from a part of the branch which comes between the lateral incisor and the canine, forms an attachment means for one of the ends of an elastic intermaxillary traction ring, the other end of which is attached to a gingival hook projecting from the housing fastened to the first mandibular molar.

This device, used in a first therapeutic stage, makes it possible to dispense with any other means for putting the arch wire under traction and, in particular, with the pericranial support means. Said device is easily inserted between the gums and the cheeks and, by virtue of the good connection between the arch wire and the grooves of the housings subjected to stress, makes it possible to reduce the straightening time.

DESCRIPTION OF THE DRAWING

Other characteristics and advantages may be gathered from the following description, with reference to the accompanying diagrammatic drawing which illustrates by way of example the various elements of an appliance according to the invention with occlusal fastening and in which:

FIG. 7 is a perspective view showing, on an enlarged scale, a housing for a maxillary canine, equipped with an axial straightening device, FIG. 8 is a partially sectional side view of the housing of FIG. 7, FIG. 9 is a perspective view similar to FIG. 7, but showing the elements of the straightening device when they are in the straightening situation, FIG. 10 is a side elevation view of a mandibular premolar equipped with its housing, FIG. 11 is a front elevation view of a tying ring equipped with its manipulating handle, FIGS. 12 to 14 are side elevation views showing different phases in the tying of an arch wire to a maxillary incisor by means of the ring of FIG. 11, FIG. 15 is an elevation view of a cluster carrying several tying rings.

DESCRIPTION OF THE PREFERRED EMBODIMENTS

Figure 1:
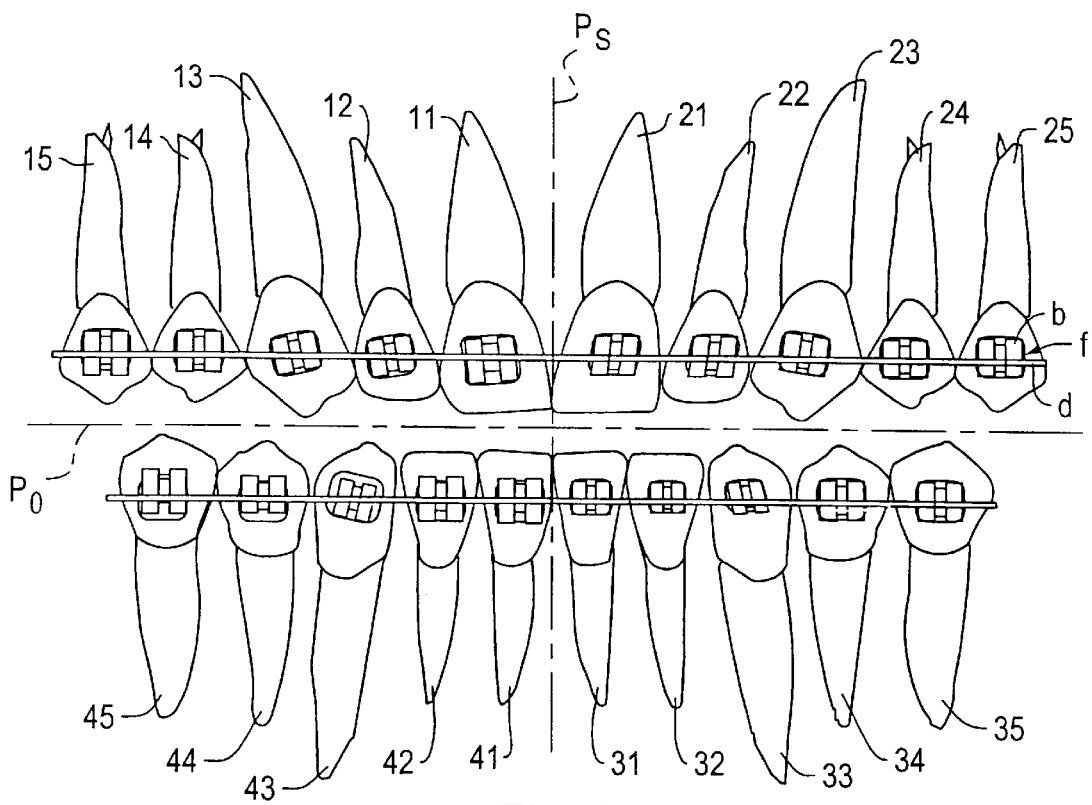
FIG. 1 is a conventional diagrammatic view of the teeth of the maxillary and mandibular arches which are equipped with an appliance of the prior art.
Figure 2:
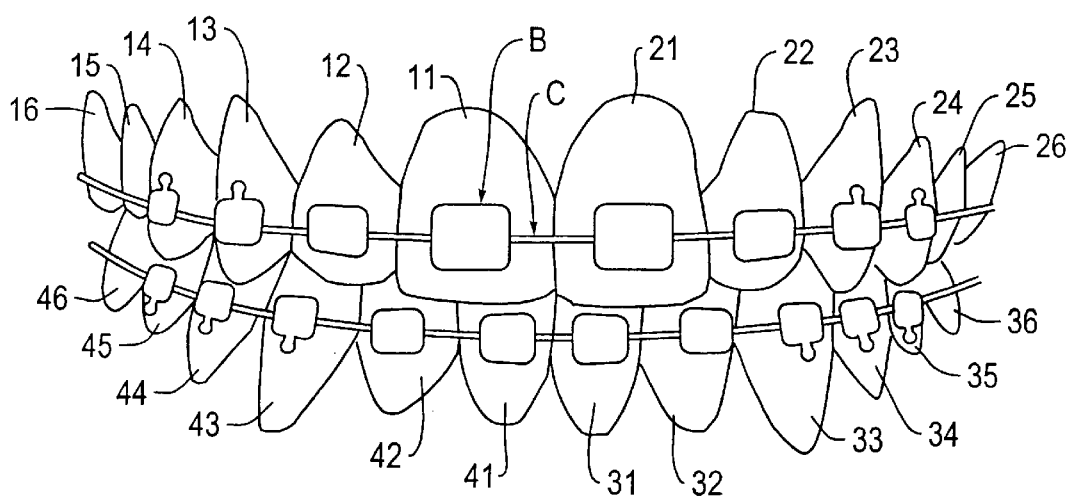
FIG. 2 is a partial perspective view from the front of an appliance according to the invention, when it is put in place on the two dental arches.

It is customary, according to the international standards relating to the representation of the two in each case maxillary and mandibular dental arches, to distribute the teeth in four quadrants delimited by the occlusal plane PO and by the sagittal plane PS, as shown in FIG. 1, and to assign to each quadrant a numbering which starts from a new decade, with this decade being assigned a unit corresponding to the position of the tooth relative to the sagittal plane. Thus, in the maxillary arch, the central incisors are designated 11 and 21, the lateral incisors 12 and 22, the canines 13, 23, the first premolars 14, 24, the second premolars 15, 25, the first molars 16, 26 and the second molars 17 and 27, the teeth of the mandibular arch being designated from 31 to 37, 41 and 47, as shown in FIGS. 1 and 2, where the representation of the teeth stops at the premolars in FIG. 1 and at the first molars in FIG. 2.

Due to this conventional numbering, in the following description the corresponding references to the elements of the invention will be numbered from 50.

Figure 16:
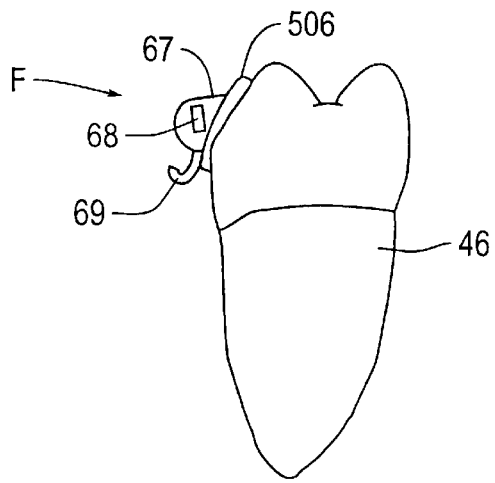
FIG. 16 is a side elevation view of a molar equipped with its housing.
Figure 17:
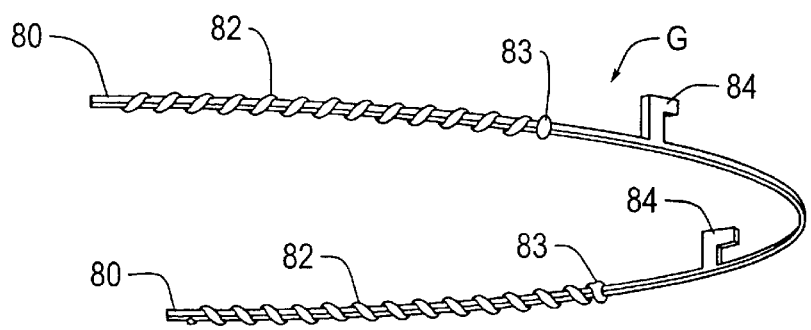
FIG. 17 is a perspective view of an arch wire with bilateral distalization.
Figure 19:
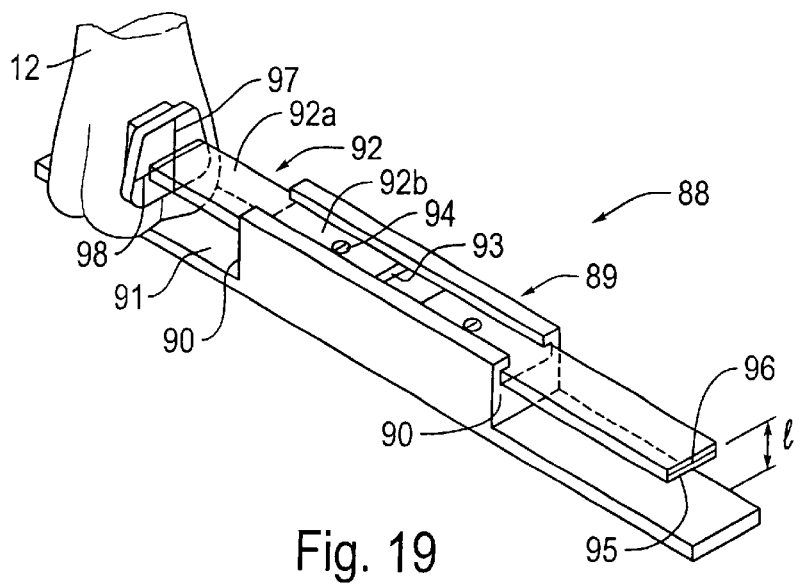
Figure 18:
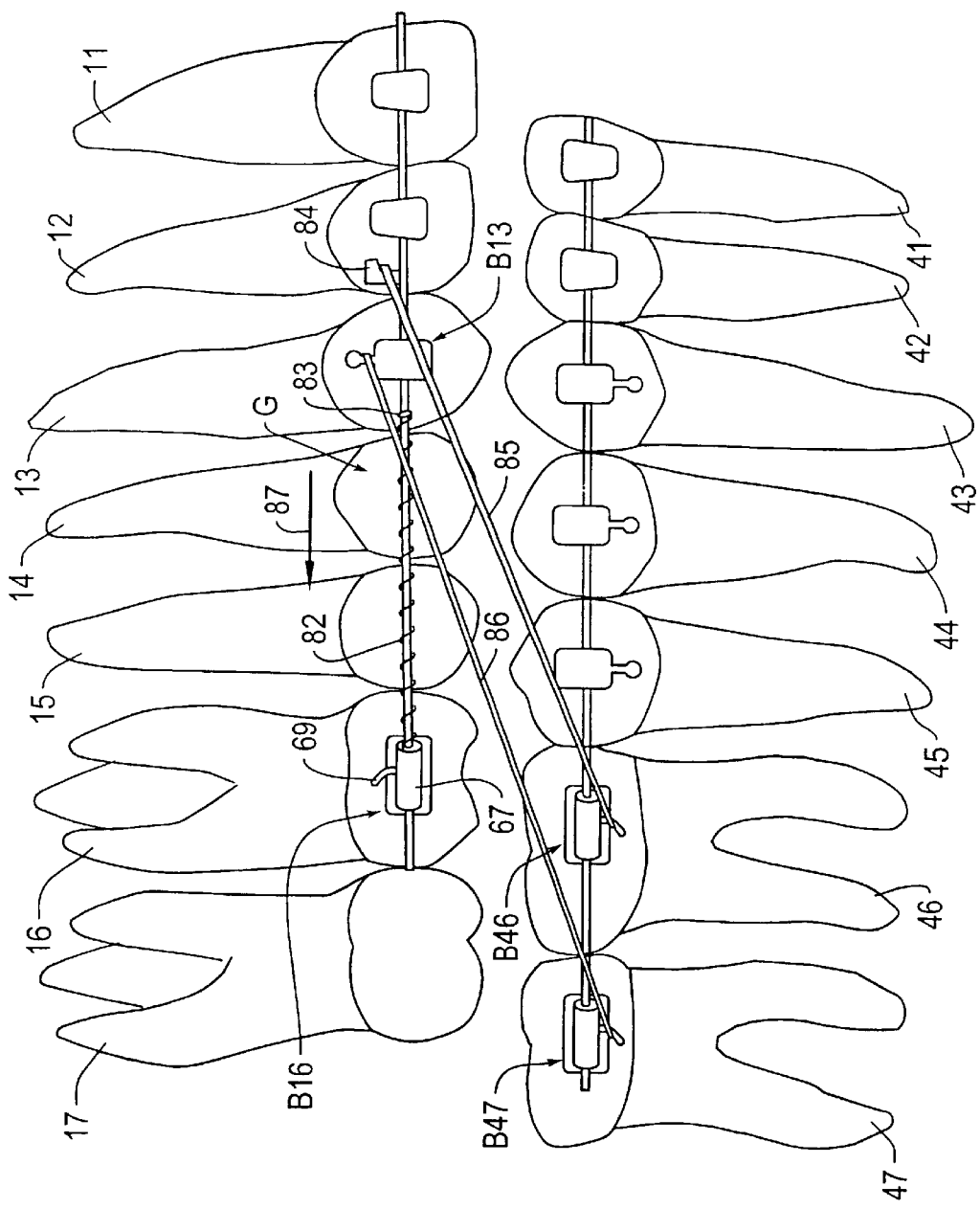
FIG. 18 is a side elevation view of a set of teeth which is equipped with the appliance having the bilateral distalization arch wire of FIG. 17, FIG. 19, is a perspective view of an embodiment of a gage for positioning a housing.

The appliance according to the invention is therefore composed of housings B, of arch wires with optional sleeves C, forming part of a series of a plurality of arch wires, of tying means E which can be seen in FIGS. 11 to 15, of a means F for positioning the ends of the arch wires, as can be seen in FIG. 16, and of distalization means G shown in FIGS. 17 and 18.

According to the invention, and as shown in FIGS. 3 to 6, each housing B for the incisors, canines and premolars is composed of a base 50 making it possible to fasten said housing by gluing to the anterior face of the tooth, of an anterior wall 51 and of an intermediate bridge 52. The housing is produced from a metal alloy and may comprise, on the outer anterior face of the wall 51, a ceramic pad 53 of the color of ivory or matching the coloration of the teeth. In the intermediate bridge 52 is made a groove 54 of rectangular cross section which issues in the direction of the occlusal plane, that is to say downward with regard to a housing for the maxillary arch and upward with regard to a housing for the mandibular arch. The intermediate bridge 52 likewise comprises, on the one hand, between the base 50 and the groove 54, an anchoring flute 55 issuing on the same side as the groove 54 and, on the other hand, between the base 50 and the wall 51, a groove 56 issuing opposite the groove 54. FIGS. 3 to 6 clearly show that the anterior wall 51, seen from the front, has a square or trapezoidal shape and has a width and a height greater than those of the bridge 52 and of the base 50 so as to mask these two parts, that is to say conceal them from view. As shown more particularly in FIGS. 5 and 6, each of the housings for the canines and the premolars comprises, furthermore, a vertical spur 57 which projects from the wall 51 on the opposite side to the groove 54, that is to say on the opposite side to the occlusal plane of the mouth.

Figure 3:
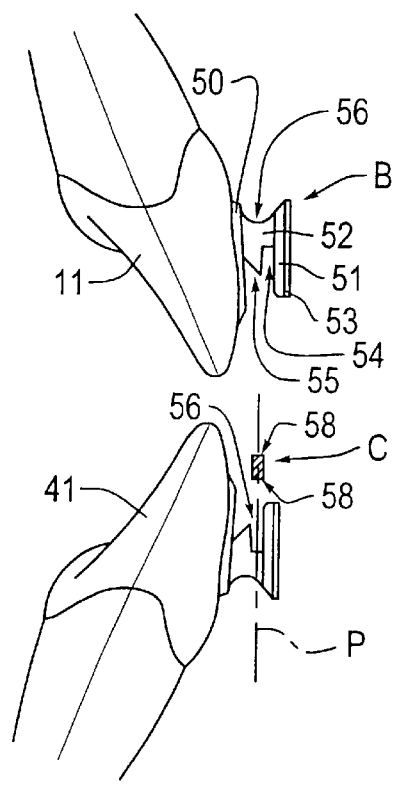
FIG. 3 is a partial side view showing the incisors equipped with their housings.

The groove 54, made in each housing, has a rectangular cross section allowing it to receive arch wires of round or square cross section, but also an arch wire of rectangular cross section, the small sides 58 of which are parallel to the occlusal plane, as shown in FIG. 3. It should be noted that, when the arch wire is engaged in the groove 54, the forces of reaction to the clamping of the teeth by the arch wire, said forces tending to cause this arch wire to bend, have no effect on this wire in its part included in the groove 54 of each housing B, since they are countered by the wall 51. The result of this is that the straightening forces imparted to the teeth by the arch wire are utilized much more effectively than in housings comprising a horizontal groove issuing to the front and thus making it possible to reduce the treatment time. The correction of the axial dental rotations is therefore highly effective.

FIGS. 7 to 9 show a therapeutic aid which can be used for treating complex pathologies for which the straightening afforded by the housings would prove inadequate in spite of the good housing/arch-wire connection.

In this embodiment, each housing for the canines and for the maxillary premolars is associated with straightening means D and comprises, in its intermediate part 52, a vertical through well 59 issuing into the horizontal groove 54 and, more specifically, into a semicircular flute 60 made in the bottom of this groove. The well 59 is cylindrical and has a diameter slightly greater than the outside diameter of the wire forming a kickover spring 62 which comprises a vertical branch 63 and a branch 64. The branches 63 and 64, at rest, form an angle u having a value of between 60 and 90°. The free end of the branch 64 is bent at 64a and folded to form a hook 65. When such a housing is placed on a maxillary canine 13 which has to be subjected to axial straightening, as soon as the connection between the housing and the tooth is sufficient the branch 63 of the spring is introduced vertically into the well 59 until the turn 61 of the spring 62 comes into abutment on the bottom of the groove 56. From that situation, the straightening of that part of the branch 63 which projects from the well 59 causes the folding of this part and its engagement in the flute 60 of the housing, thus ensuring the connection of the kickover spring 62 to this housing. After the arch wire C has been put in place, in order to impart a straightening torque to the housing and to the tooth it is sufficient for the branch 64 to be brought closer to the branch 63, until the hook 65 comes above the arch wire C, and then to release the branch 64 in such a way that this hook hooks onto the arch wire, as shown in FIG. 9.

It will be noted that, in this configuration, with the exception of the metal branch 64, all the other elements of the straightening means are concealed behind the wall 51 of the housing.

FIG. 10 shows that, with regard to the maxillary and mandibular premolars, the intermediate bridge 52 and the anterior wall 51 are shifted in the direction of the root of the tooth in relation to their base 50a which is then wider. This eliminates the risks of occlusal interference with the premolars facing one another and gives the housing better stability by changing the level and height of the gluing of its base to the tooth. The jutting of the base 50a, which is of small amount, has little influence on the general esthetic appearance of the appliance, the more so because the housing in question can scarcely be seen.

Finally, FIG. 16 shows that each housing for the molars is composed of a base 50b, from which projects a step 67, through which passes a tunnel 68 having a cross section of the same shape and dimensions, apart from the functional play, as those of the arch wire having the maximum transverse dimensions. The step is also integral with a gingival hook 69 making it possible to attach a conventional intermaxillary connection.

Figure 5:
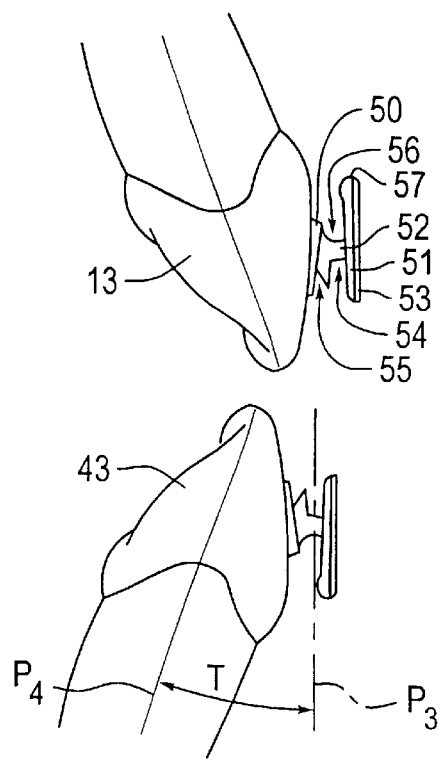
FIG. 5 is a partial side view showing the canines equipped with their housings.
Figure 4:
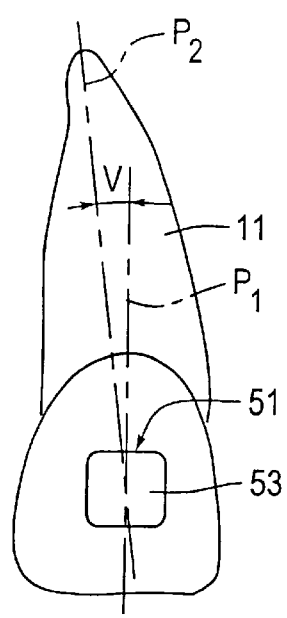
FIG. 4 is a front view of the maxillary incisor of FIG. 3.
Figure 6:
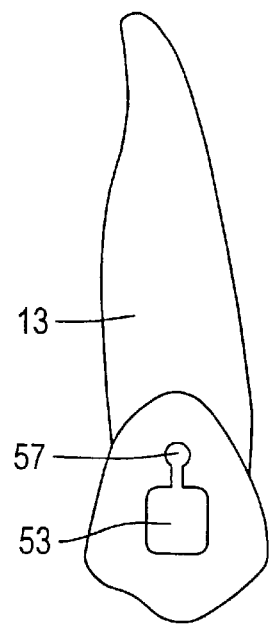
FIG. 6 is a front elevation view of the maxillary canine of FIG. 5.

In a known way, and as shown in FIG. 4, in each of the housings thus described, the midplane P1 of the housing, hence of the groove 54, forms, relative to the midplane P2 of the tooth onto which it has to be placed, an angle V having a variable value, depending on the teeth. Likewise, as shown in FIGS. 5 and 16, the midplane P3 of the groove 54 or of the tunnel 68 forms, relative to the midplane P4 of the tooth, an angle T, the value of which varies, depending on the tooth in question.

The accompanying table indicates by way of example the values given to these various angles for each of the housings, with a reminder of the characteristics of each housing.

The appliance is put in place by first gluing the housings to the front face of the teeth in question, either as having to be oriented or so as to serve as a support. This gluing is preceded by accurate positioning which is carried out by means of a positioning gage designated as a whole by 88 in FIG. 20.

This gage consists of a bar 89 which, made of sterilizable material, comprises, projecting from at least one of its end faces 90, a spatula 91 for bearing on the top of a tooth. The spatula 91 is associated with a blade 92 which is parallel to it and which comprises a part 92a projecting from the bar and a part 92b engaged in a slideway 93 of this bar. The blade is produced from sterilizable transparent synthetic material. It is interchangeable and, where appropriate, can be discarded.

If appropriate, a screw 94 ensures that said blade is fixed to the bar. The blade end face 95, which is set back from that of the spatula 91, comprises a horizontal line 96 which is colored or not. The distance 1 between the line 96 and the face 91a of the spatula 91 is, of course, adapted to the housing B which, in turn, is specific to a type of tooth. The value of 1 is, for example:

- 3.5 mm for the maxillary lateral incisors and the second premolars,
- 4 mm for the maxillary and mandibular central incisors and for the first premolars,
- 4.5 mm for the mandibular canines,
- and 5 mm for the maxillary canines.

To reduce the number of gages, each bar 89 comprises, at each of its ends, a spatula 91/blade 92 assembly suitable for a positioning measurement. Thus, two bars are sufficient for ensuring the four positioning measurements of all the housings.

To position a housing B12 on a maxillary lateral canine 12, this housing is previously provided, on its anterior face, with an erasable cross formed by a vertical stroke 97 and a horizontal stroke 98. After the glue for fastening the housing to the tooth has been put in place and while this glue still allows the housing to be displaced, the latter is first positioned transversely, by its vertical stroke 97 being brought substantially into the vertical midplane of the tooth, and is then positioned vertically by means of the gage 88.

After the spatula 91 has been placed onto the tooth, the orthodontist displaces the housing until its horizontal stroke 98 coincides with the line 96 of the blade. This adjustment is made easier by the fact that the blade 92 is transparent. At this stage, the positioning gage is removed.

When all the elements are positioned and fastened, the ties E are put in place, and then the arch wires C are introduced first into the tunnels 68 of the housings fastened to the molars and then into the horizontal grooves 54 of each of the housings. This engagement is carried out very easily, whatever the cross sections of the arch wire used and the elasticity of the branches of this wire. This arrangement takes place from the bottom upward with regard to the maxillary housings and from the top downward as regards the mandibular housings. When the mandibular wires are fitted, if the appliance comprises straightening means D, the hooks 65 are put in place and then tying means are fitted.

In order to make this putting in place easier and according to one characteristic of the invention, each tying ring 70, which is produced from elastic synthetic material, for example from elastomer, is integral with a gripping handle 71, to which it is connected by means of a breakable zone 72. This assembly is supplied in the form of a cluster 73 composed of a main branch 74, on either side of which are arranged transversely the handles 71 connected to this branch by means of breakable zones 75.

As a result of this arrangement, each ring 70 can be gripped very easily by its handle 71 in order to be detached from the cluster 73 and be brought around the intermediate bridge 52 and into the grooves 56 and 55 of each housing in question, as shown in FIG. 12, this taking place before the arch wire C is put in place. After this arch wire has been put in place, and as shown in FIG. 13, the orthodontist can, without difficulty, by grasping the gripping handle 71, cause the ring 70 to pivot about the arch wire C in order to attach its loop, up to then at the bottom, in the groove 56, as shown in FIGS. 13 and 14, thus forming a double tie. As soon as the tie is completed, the handle 71 is separated from the ring by the severing or breaking of the zone 72. FIG. 14 shows that the ring 70 is inserted completely behind the wall 51.

This tie, having a double passage, forms two loops which, arranged on either side of the bridge 52, surround the parts of the wire which emerge from the groove 54. These loops ensure that the wire is wedged in terms of vertical translation against the bottom of the groove 54, is wedged in terms of horizontal translation against one of the vertical walls of the groove, if there is play, and is wedged in terms of longitudinal translation. Thus, the arch wire C is connected to the housing firmly and positively, so that the latter cannot pivot relative to this wire. The result of this is that the straightening force can impart to the tooth only a translational force parallel to itself which is conducive to straightening.

The arch wires may be made of steel or of any other alloy combining nickel and titanium or titanium and molybdenum, in the same way as in form memory alloys or composite material. Advantageously, in the gaps between housings, they receive sleeves made of synthetic material which have the color of the teeth. Under these conditions, the entire front part of the appliance has the color of the teeth and considerably improves the esthetic appearance of the mouth.

As an example, the arch wires have, depending on their cross section, the following dimensions expressed in millimeters:

- round cross section; diametral dimension 0.304 mm; 0.355 mm; 0.406 mm; 0.457 mm and 0.508 mm
- square cross section: 0.508 mm×0.508 mm and 0.558 mm×0.558 mm
- rectangular cross section for vertical insertion with the narrow side horizontal: 0.558 mm×0.406 mm; 0.635 mm×0.482 mm and 0.635 mm×0.508 mm.

In an embodiment shown in FIGS. 17 and 18, the maxillary arch wire intended for ensuring bilateral distalization comprises, on each of its branches 80, a helical spring 82 which is arranged around said branch. Each spring is fixed to the branch by means of a weld 83 of its anterior end. This weld is made in that zone of the branch which is set back from the canines. This arch wire also comprises a vertical hook 84 which projects toward the top of the branch part which comes between the incisor and the lateral canine. The position of the spurs on the branches 80 depends on the patient's morphology as does, moreover, the position of the stop welds 83. In other words, this type of arch wire is supplied in several models which differ in the shape of the arc and in the position of the hooks 84 and of the welds 83.

This arch wire for active distalization is used in a first treatment stage for distalizing the molars and the canines. It implies that the premolars are not provided with any housing, as shown with regard to those 14 and 15 in FIG. 18. This figure also shows that this arch wire is employed with a maxillary arch comprising on the molar 16 a housing B16 and on the mandibular arch housings B46 and B47 of the type illustrated in FIG. 16. The maxillary arch is equipped with a housing for a canine B13, of the type illustrated in FIGS. 5 and 6.

When the two arch wires are positioned, two elastic intermaxillary traction ties are put in place on each side of the appliance, to be precise a tie 85 extending from the hook 84 to the hook 69 of the housing B46 and a tie 86 extending from the hook 57 of the housing B13 fastened to the canine to a hook 69 of a housing B47 fastened to the molar 47. The arch wire is subjected by these ties to a tensile force in the direction of the arrow 87 which brings the free end of its spring 82 to bear under compression against the step 67 of the housing B16 and thus imparts a distalizing force to the molar 16. This original mechanism for distalizing the teeth avoids the orthodontic extractions of healthy premolars normally prescribed to make room posteriority in patients who have "protruding teeth".

Although this device is partially visible in the first treatment phase, it is much less demanding for the patient than an extra-oral appliance and, in particular, an appliance with pericranial support.

It may be gathered from the foregoing that the appliance according to the invention not only makes the practitioner's work easier and improves the esthetic appearance of the patient, but also, by virtue of the high stability of the arch wires in the housings, improves the straightening of the teeth and consequently makes it possible to reduce the treatment time, while at the same time improving dental hygiene.

Table of the individual technical characteristics of the housings

|  | Angulation under torsion T | Axial angulation V | Housings | Horizontal angulation |
|---|---|---|---|---|
| Maxillary teeth |  |  |  |  |
| Central incisors 11 and 21 | 22° | +5° | Simple housing | No |
| Lateral incisors 12 and 22 | 14° | +8° | Simple housing | No |
| Canines 13 and 23 | 5° | +10° | Simple housing + straightening spring | No |
| 1st premolars 14 and 24 | 0° | 0° | Simple housing | No |
| 2nd premolars 15 and 25 | −7° | 0° | Simple housing | No |
| 1stt molars 16 and 26 | −10° | 0° | Tunnel + hook | 10° |
| 2nd molars 17 and 27 | −10° | 0° | Tunnel + hook | 6° |
| Mandibular teeth |  |  |  |  |
| Central incisors 31, 32, 41, 42 | −6° | 0° | Simple housing | No |
| Lateral incisors 33 and 43 | −7° | +6° | Simple housing | No |
| 1st premolars 34 and 44 | −11° | 0° | Simple housing | No |
| 2nd premolars 35 and 45 | −17° | −3° | Simple housing | No |
| 1st molars 36 and 46 | −22° | −6° | Cast tunnel + hook | 6° |
| 2nd molars 37 and 47 | −27° | −10° | Cast tunnel + hook | 10° |

What is claimed is:

1. An orthodontic dental kit which, for each in each case maxillary and mandibular dental arch, comprises:
    a series of arch wires forming a U-shaped arc, adaptable to surround each dental arch and differing from one another in the straightening forces which their branches supply, said wires having a rectangular cross section with their small sides parallel to the occlusal plane,
    metal housings adaptable to be fastened by their base being glued to the incisors, canines and premolars and comprising a horizontal groove for receiving the arch wire, said groove issuing in the direction of the occlusal plane and being formed in an intermediate bridge connecting the base to an anterior wall,
    metal housings adaptable to be fastened by gluing to the molars and comprising a tunnel for positioning the end of the corresponding branch of the arch wire,
    ties, for tying the arch wire in the grooves of the housings,
    and means imparting, at least to the maxillary arch wire and in one treatment phase, a tensile force directed toward the rear, wherein each of the housings for the incisors, canines and premolars comprises, for connecting to the arch wire, and in the intermediate bridge, on one side, between the base and the groove for the arch wire, an anchoring flute issuing in the direction of the occlusal plane and, on the other side, between the base and the anterior wall, a horizontal groove issuing opposite the groove for the arch wire, while the anterior wall has a width and a height greater than those of the base and those of the intermediate bridge, in order to mask this bridge and the connection to the arch wire.

2. The appliance as claimed in claim 1, wherein the connection is by an elastic ring.

3. The appliance as claimed in claim 2, wherein the tie formed by the elastic ring comprises two loops surrounding the parts of the arch wire which project longitudinally from the intermediate bridge, and these loops are obtained as a result of the elastic ring being put in place around the intermediate bridge in the flute and in the groove of the housing, then, after the introduction of the arch wire into the groove, of the ring being pivoted around the arch wire for the purpose of attaching its loop coming from the flute in the opposite groove.

4. The appliance as claimed 2, wherein the elastic ring is made of elastomer and is connected by a breakable zone to a manipulating handle, itself connected by a breakable zone to the central branch of a cluster, said cluster being composed of a plurality of handle/ring assemblies distributed on either side of its central branch.

5. The appliance as claimed in claim 1, wherein each housing for the canines and premolars comprises, in its part between the base and the anterior wall, a vertical well issuing into the groove for the arch wire and forming, with a flute made in the bottom of said groove, an anchoring member for the bent end of one of the branches of a kickover spring for the axial straightening of the tooth, the other branch of this spring being provided with an end hook hooking onto the arch wire.

6. The appliance as claimed in claim 1, wherein the anterior face of the anterior wall of each housing for the incisors, canines and premolars is covered by a pad having a color close to that of the teeth.

7. The appliance as claimed in claim 6, wherein each of the in each case maxillary and mandibular arch wires is surrounded, in the gaps between housings, by sleeves made of synthetic material having the color of the teeth.

8. The appliance as claimed in claim 1, which comprises a maxillary arch wire for the bilateral distalization of the molars and canines, comprising on each of its lateral branches, on the one hand, a helical spring which is arranged around said branch and the anterior end of which is connected to this branch by means of a weld arranged on a zone of this branch which is set back from the canine, while the posterior end of this spring comes to bear on the housing of the molar to be straightened, and, on the other hand, a vertical hook which, projecting upward and from that part of the branch which comes between the lateral incisor and the canine, forms an attachment means for one of the ends of an elastic intermaxillary traction ring, the other end of which is attached to the hook of the housing fastened to the corresponding first mandibular molar.

9. The appliance as claimed in claim 1, wherein each housing comprises, on its anterior face, an erasable centering cross composed of a vertical stroke and of a horizontal stroke and capable of cooperating with a positioning gage, while said gage is composed, on the one hand, of a bar, at least one of the end faces of which is prolonged by a spatula for bearing on the tooth, and, on the other hand, of an interchangeable blade which, parallel to the spatula, is shorter than the latter, projects from the same end face, is produced from a transparent material and comprises, on its end face, a horizontal line for positioning the horizontal stroke of the housing.

* * * * *